United States Patent
Radulescu et al.

(10) Patent No.: US 10,929,951 B2
(45) Date of Patent: *Feb. 23, 2021

(54) ANATOMICALLY INTELLIGENT ECHOCARDIOGRAPHY FOR POINT-OF-CARE

(71) Applicant: KONINKLIJKE PHILIPS N.V., Eindhoven (NL)

(72) Inventors: Emil George Radulescu, Ossining, NY (US); Ivan Salgo, Pelham, MA (US); Sheng-Wen Huang, Ossining, NY (US); Ramon Quido Erkamp, Swampscott, MA (US); Shougang Wang, Ossining, NY (US); Irina Waechter-Stehle, Hamburg (DE); Christian Buerger, Hamburg (DE); Sabine Mollus, Juelich (DE); Juergen Weese, Norderstedt (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

This patent is subject to a terminal disclaimer.

(21) Appl. No.: 16/553,211

(22) Filed: Aug. 28, 2019

(65) Prior Publication Data
US 2020/0043129 A1 Feb. 6, 2020

Related U.S. Application Data

(63) Continuation of application No. 14/652,317, filed as application No. PCT/IB2013/060908 on Dec. 13, 2013, now Pat. No. 10,424,044.

(Continued)

(51) Int. Cl.
*G06T 3/00* (2006.01)
*G06T 7/10* (2017.01)
(Continued)

(52) U.S. Cl.
CPC ............... *G06T 3/00* (2013.01); *A61B 8/085* (2013.01); *A61B 8/0883* (2013.01); *A61B 8/42* (2013.01);
(Continued)

(58) Field of Classification Search
CPC .... G06T 3/00; G06T 7/10; G06T 7/75; G06T 7/0012; G06T 2207/10132;
(Continued)

(56) References Cited

U.S. PATENT DOCUMENTS

| | | | |
|---|---|---|---|
| 5,529,070 A | 6/1996 | Augustine | |
| 5,906,578 A * | 5/1999 | Rajan | A61B 8/5223 600/424 |

(Continued)

FOREIGN PATENT DOCUMENTS

JP 2010088584 A 4/2010

OTHER PUBLICATIONS

PCT International Search Report, International application No. PCT/IB2013/060908, dated May 9, 2014.

*Primary Examiner* — Maria E Vazquez Colon

(57) ABSTRACT

An apparatus includes an imaging probe and is configured for dynamically arranging presentation of visual feedback for guiding manual adjustment, via the probe, of a location, and orientation, associated with the probe. The arranging is selectively based on comparisons between fields of view of the probe and respective results of segmenting image data acquired via the probe. In an embodiment, the feedback does not include a grayscale depiction of the image data. Coordinate system transformations corresponding to respective comparisons may be computed. The selecting may be based upon and dynamically responsive to content of imaging being dynamically acquired via the probe.

12 Claims, 9 Drawing Sheets

Related U.S. Application Data

(60) Provisional application No. 61/740,595, filed on Dec. 21, 2012.

(51) Int. Cl.

| | | |
|---|---|---|
| *G06T 7/73* | (2017.01) | |
| *A61B 8/08* | (2006.01) | |
| *A61B 8/00* | (2006.01) | |
| *G01S 7/52* | (2006.01) | |
| *G01S 15/89* | (2006.01) | |
| *H04N 5/232* | (2006.01) | |
| *G06T 7/00* | (2017.01) | |
| *H04N 7/18* | (2006.01) | |
| *A61B 8/06* | (2006.01) | |

(52) U.S. Cl.
CPC ............ *A61B 8/4254* (2013.01); *A61B 8/461* (2013.01); *A61B 8/52* (2013.01); *G01S 7/52036* (2013.01); *G01S 7/52073* (2013.01); *G01S 7/52076* (2013.01); *G01S 7/52084* (2013.01); *G01S 15/8915* (2013.01); *G01S 15/8993* (2013.01); *G06T 7/0012* (2013.01); *G06T 7/10* (2017.01); *G06T 7/75* (2017.01); *H04N 5/23293* (2013.01); *H04N 5/232939* (2018.08); *H04N 7/18* (2013.01); *A61B 8/065* (2013.01); *A61B 8/0858* (2013.01); *A61B 8/429* (2013.01); *A61B 8/4427* (2013.01); *A61B 8/4455* (2013.01); *A61B 8/483* (2013.01); *A61B 8/5223* (2013.01); *A61B 2576/023* (2013.01); *G06T 2207/10132* (2013.01); *G06T 2207/30048* (2013.01)

(58) Field of Classification Search
CPC .... G06T 2207/30048; H04N 5/232939; H04N 5/23293; H04N 7/18; A61B 8/085; A61B 8/0883; A61B 8/42; A61B 8/4254; A61B 8/461; A61B 8/52; A61B 8/065; A61B 8/0858; A61B 8/429; A61B 8/4427; A61B 8/4455; A61B 8/483; A61B 2576/023; G01S 7/52036; G01S 7/52073; G01S 7/52076; G01S 7/52084; G01S 15/8915; G01S 15/8993

See application file for complete search history.

(56) References Cited

U.S. PATENT DOCUMENTS

| | | | |
|---|---|---|---|
| 5,952,577 | A | 9/1999 | Passi |
| 6,299,579 | B1 | 10/2001 | Peterson |
| 7,933,007 | B2 | 4/2011 | Stanton |
| 2004/0019270 | A1* | 1/2004 | Takeuchi ............ G06F 19/321 600/407 |
| 2004/0193042 | A1 | 9/2004 | Scampini |
| 2005/0096539 | A1 | 5/2005 | Leibig |
| 2006/0004290 | A1 | 1/2006 | Smith et al. |
| 2007/0016005 | A1 | 1/2007 | Timinger |
| 2007/0167760 | A1 | 7/2007 | Kim |
| 2008/0221446 | A1 | 9/2008 | Washburn |
| 2008/0260254 | A1 | 10/2008 | Schramm |
| 2009/0141957 | A1 | 6/2009 | Yen |
| 2009/0202150 | A1* | 8/2009 | Fradkin ................ G06T 7/149 382/173 |
| 2010/0168556 | A1 | 7/2010 | Shen |
| 2010/0217123 | A1* | 8/2010 | Eran ..................... A61B 8/08 600/437 |
| 2010/0324422 | A1 | 12/2010 | Wanda |
| 2011/0246129 | A1* | 10/2011 | Ishikawa ............ A61B 8/463 702/150 |

\* cited by examiner $$\rho(r,\theta) \equiv \frac{C[b_1(r,\theta),b_2(r,\theta)]}{\sqrt{C[b_1(r,\theta),b_1(r,\theta)]}\sqrt{C[b_2(r,\theta),b_2(r,\theta)]}}$$

where $$C[b_k(r,\theta),b_l(r,\theta)] \equiv \int_{-\infty}^{\infty}\int_{-\infty}^{\infty} w(r',\theta')b_k(r+r',\theta+\theta')b_l(r+r',\theta+\theta')dr'd\theta'$$

and where $$b_k(r,\theta) = \sum_{j \in C_k} s_j(r,\theta)$$

ANATOMICALLY INTELLIGENT ECHOCARDIOGRAPHY FOR POINT-OF-CARE

RELATED APPLICATIONS

This is a Divisional of U.S. application Ser. No. 14,652,317, filed Jun. 15, 2015, which claims priority to PCT Application PCT/IB2013/060908, filed Dec. 13, 2013, which claims priority to the US Application No. 61/740,595, filed Dec. 21, 2012, the contents of which are incorporated herein by reference.

FIELD OF THE INVENTION

The present invention relates to user guidance in adjusting imaging probe location and orientation and, more particularly, to the guidance being visual.

BACKGROUND OF THE INVENTION

Heart failure is a major disease with five million patients in the United States alone and tens of millions worldwide. The individuals at risk of heart failure are estimated at 60 million in the United States only; one million are hospitalized, the rest being in the care of heart failure clinics. Basic information about the heart is needed in the heart failure clinics or general practitioners' offices for patient management. This information includes images as well as quantification data, such as ejection fraction, computed from the image once the image is acquired. Ultrasound is a reliable and cost-effective imaging modality for soft tissue such as the heart.

Acquisition of an ultrasound image requires a skilled sonographer. One parameter the sonographer, or other clinician trained in sonography, optimizes is the field of view. The apical four chamber view is a standard one for routine cardiac checkups. The clinician places the head of the ultrasound probe, or "transducer probe", on the patient. An effective site on the patient's skin for placement of the probe for various views is part of the clinician's training, and the site can vary from patient to patient. For the apical four chamber view the probe is placed over the apex of the heart. The probe also needs to be manually tilted, typically in different directions until the organ is captured for imaging. This is all done interactively, with the clinician viewing the image, which is usually a sonogram, on-screen. Interpreting a sonogram is a skill that must be developed, e.g., through training and practice. The clinician's experience tells him or her, in an ongoing iterative process, how to shift and tilt the probe to achieve an effective acoustic window.

SUMMARY OF THE INVENTION

What is proposed herein below is directed to addressing one or more of the above concerns.

Access to a full ultrasound scan in heart failure clinics and general practitioner's offices is not easy. Making the ultrasound system portable would help. However, although most cardiologists would be able to use a conventional portable ultrasound system, they are generally too busy to carry out this procedure themselves.

Yet, serial imaging, in which images of the heart are taken periodically for example, would improve patient treatment.

What is needed is a point-of-care solution that enables automatic ultrasound-based volumetric measurement of the heart during the patient's regular visit, which would be especially useful in heart failure clinics. A nurse trained in placing ECG leads, but with no training in echocardiography, would operate the portable system and the cardiologist would be provided with the diagnostic images together with automatic measurements such as ventricle size and ejection fraction.

Such a technology would lower the barrier to use of ultrasound data for cardiac diagnostic and follow-up examinations.

In accordance with an aspect of the present invention, an apparatus includes an imaging probe. It further includes a user-guidance processor configured for dynamically arranging presentation of visual feedback for guiding manual adjustment, via the probe, of a location, and orientation, associated with the probe. The arranging is selectively based on comparisons between fields of view of the probe and respective results of segmenting image data acquired via the probe.

In a sub-aspect, the arranging includes presenting the feedback. The feedback includes user instructions on manually maneuvering the probe.

In a further sub-aspect, the feedback does not include a grayscale depiction of image data acquired via the probe.

In another sub-aspect, the apparatus is configured for computing coordinate system transformations corresponding to respective ones of the comparisons.

In a first further sub-aspect, the computing is dynamically based on the results.

In a second further sub-aspect, the selecting is respectively based on magnitudes of translational and rotational components of the transformations.

In a third further sub-aspect, the computing is responsive to respective pauses in the adjusting.

In a relevent sub-aspect, the probe includes a sensor. The apparatus is configured for deciding, based on output of the sensor, that acoustic coupling quality is insufficient and for issuing a user alert upon the decision.

In a related sub-aspect, the segmenting is model-based.

In an associated sub-aspect, the selecting is based upon and dynamically responsive to content of imaging being dynamically acquired via the probe.

In a particular sub-aspect, the imaging probe is or includes an ultrasound imaging probe.

In a more overall sub-aspect, the presenting dynamically guides a user in a procedure for achieving an apical view of a heart.

As an added sub-aspect, at least one of the fields of view is three-dimensional.

In a different sub-aspect, the acquiring of the image data to be segmented occurs respectively from the fields of view.

In a specific sub-aspect, a field of view from among the fields of view has a viewpoint coinciding with the location. The orientation coincides with a viewing orientation of the field of view.

From an implementational sub-aspect, the apparatus further comprises a display and a user-operable console. The apparatus is configured for: a) acquiring the image data via the probe b) the segmenting c) displaying the feedback via the display; and d) portability, as a hand-carriable unit.

In still another sub-aspect, issuing a user alert for halting the adjustment is responsive to content of imaging dynamically acquired via the probe.

As a further sub-aspect, the apparatus is configured for detecting the halting.

In a yet, further sub-aspect, the apparatus is further configured for, responsive to detecting that the halting has occurred, performing the segmenting.

In one other particular sub-aspect, the apparatus is configured for the segmenting in a relatively coarse mode and in a relatively fine mode. It is further configured for making a volumetric measurement based on one or more segments formed as a result of the spatially finer segmenting. Making the measurements is responsive to completion of the spatially finer segmenting.

In still one more sub-aspect, an instruction to halt, as part of the feedback, is subject to an outcome of a comparison between a current location, and current orientation, of the probe and a location and orientation derived from the segmenting.

In a similar sub-aspect, the feedback includes a progressive indicator of overall progress in acquiring a target view.

Details of the novel, real-time, user-pause-driven, acoustic-window identification guidance technology are set forth further below, with the aid of the following drawings, which are not drawn to scale.

DETAILED DESCRIPTION OF EMBODIMENTS

Figure 1:
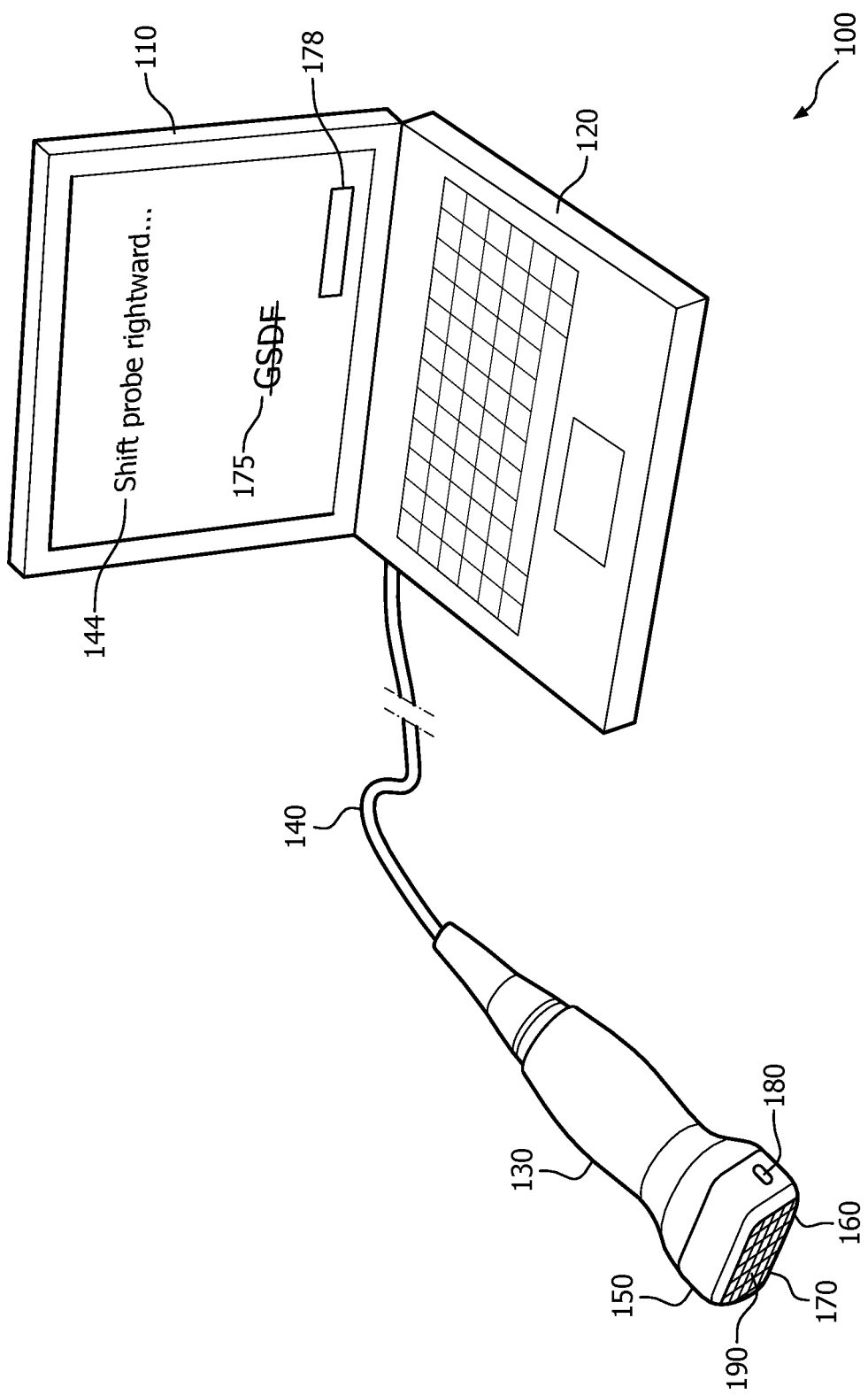
FIG. 1 is a perspective view of one form of portable apparatus in accordance with the present invention.

FIG. 1 depicts a portable apparatus 100 as one example of an implementation of the novel, real-time, user-pause-driven, acoustic-window identification guidance technology proposed herein. Although shown here in a form factor easily transportable from room to room in a clinical environment, the apparatus 100 may instead be implemented as a stationary device. The apparatus 100 includes a display 110, a user console 120, a transthoracic echocardiography (TTE) probe 130, and a probe cable 140 of extended length as represented by the broken lines in FIG. 1. The display 110 and user console may be similar to those used in a laptop computer. At a total weight of about 10 pounds, the unit 100 can be carried by hand. The description below will assume an ultrasound system, although any kind of hand-steered, imaging-probe-based system is within the intended scope of the invention. Also, although volumetric quantification and live three-dimensional imaging are features of the embodiment below, what is proposed herein applies also to two-dimensional imaging.

The apparatus 100 is configured for using ultrasound to perform volumetric imaging, such as computing the size of the left ventricle of the heart or computing ejection fraction. The computation results are stored in a memory (not shown). Live imaging acquired via the probe 130, and upon which the computations are based, is also stored in memory. Circuitry (not shown) for standard functions such as dynamic beamforming, scan conversion and image rendering is also included within the apparatus 100. Two or more beamformers can be included for automatic image blockage detection, which is discussed further below. Additional circuitry (not shown) includes a user-guidance processor configured for dynamically presenting visual feedback, i.e., user instructions. They are of a kind specifically for guiding manual adjustment, via the probe 130, of a location and orientation associated with the probe, and accordingly an acoustic window. The processor dynamically arranges the presentation, and selectively arranges it for guiding the user and in conformity with "updates" to respective three-dimensional fields of view. The update is a new field of view, one that is suggested by one or more segments created by segmenting an image in the current field of view of the probe. The model upon which the segmentation is based provides the new field of view, based on an orientation and position of the segment(s). This new field of view, when compared to the current field of view of the probe, serves as the guidepost in notifying the clinician, untrained in sonography, on how to next manipulate the probe 130. The processor issues all instructions to the user on how to manually maneuver the probe 130 to iteratively achieve the optimal acoustic window.

Segmentation need not be as detailed for the above-described "steering" of the field of view as it is for quantification once the target acoustic window is achieved. An example of model-based segmentation that uses coarse and fine meshes is found in commonly-assigned U.S. Patent Publication Number 2009/0202150 to Fradkin et al. ("Fradkin"). The adaptation termination criterion in Fradkin can be set to keep segmentation coarse for field-of-view steering in the present embodiment of apparatus 100, or set to proceed to fine segmentation for volumetric-data-based quantification in the present embodiment. Steering and quantification are discussed further below.

In order to locate an image for segmentation, the apparatus 100 is further configured for performing a generalized Hough transform (GHT). A method for performing a GHT is discussed in commonly-assigned U.S. Patent Publication No. 2008/0260254 to Schramm et al.

The entire disclosure of both publications is incorporated herein by reference.

The apparatus 100 further has the capability of detecting motion of the probe 130. The user will often pause movement of the probe so that image segmentation can occur. Also, the apparatus 100 will check on whether an instruction to pause, e.g., because the probe 130 is close to attaining a target acoustic window, has yet been followed. In one embodiment, the apparatus 100 includes the increment calculator 80 disclosed in commonly-assigned U.S. Pat. No. 5,529,070 to Augustine et al ("Augustine"). The increment calculator 80 is supplied values by means of the probe cable 140 that originate from accelerometers (not shown) residing in the probe 130. Unlike in Augustine, the positional readings need not be matched with image acquisition. So, the increment calculator can be simplified to merely detect movement in location and/or orientation of the probe 130. The accelerometers can be apportioned between the distal and proximal parts of the probe 130, as seen from FIGS. 4, 5 and 5a of Augustine. The entire disclosure in Augustine relating to the accelerometer embodiment is incorporated herein by reference. Alternatively, an example of using electromagnetic (EM) sensors in tracking a medical tool is provided in commonly-owned U.S. Pat. No. 7,933,007 to Stanton et al. A similar system which also attaches to the tool an optical sensor is disclosed in commonly-owned U.S. Patent Publication No. 2010/0168556 to Shen et al. Motion may also be sensed by comparing successive real time images as described in commonly-owned U.S. Pat. No. 6,299,579 to Peterson et al. All three documents are incorporated herein by reference in their entirety.

The above functions for which the apparatus 100 is configured may be implemented with any suitable and known combination of software, firmware and hardware. The user-guidance processor may be realized, for example, on a device having one or more integrated circuits, or as a suitably programmed computer readable medium.

The probe 130 has a head 150 containing a matrix array 160 that includes transducer elements 170. Although, for simplicity, a relatively small number of elements 170 are shown in FIG. 1, the number might typically be in the thousands. Also, although the array 160 is shown as generally rectangular, it might be square, circular, oval or in another shape. It also might be flat, as in a linear array, or curved, as in a sector array.

Shown for purposes of illustration, on the display 110, is visual feedback 144 of kind specifically for guiding manual adjustment, via the probe 130, of the array's location and orientation. Advantageously, a user untrained in sonography need not rely on grayscale images, such as sonograms, for guidance. So, there is no reliance on a grayscale display function (GSDF), as represented by the on-screen annotation 175 that is struck out and depicted in FIG. 1. In particular, the visual feedback 144 of the embodiment shown in FIG. 1 does not include a grayscale depiction of image data acquired via the probe 130. Another example of visual feedback 144 is the on-screen overall progress bar 178. It can be annotated with a percentage such as "82%" or it can be progressively filled in and bordered by a frame that represents 100%, i.e., completion.

The probe 130 also has a pair of pause/go indicator lights 180 (one of which is visible in FIG. 1, with the other on the opposite side of the probe) realizable as a red/green light-emitting diodes (LEDs). When green, the light 180 indicates that the user should look to the display 100 for directions and then proceed by moving the probe 130 as instructed. When red, the light 180 indicates that the user should pause movement of the probe 130. Both lights are concurrently the same color.

As an alternative for the lights 180, or as an implementation of additional lights, directional indicator lights can be provided. In this alternative embodiment, when one light is green, the other is red. When green, the light indicates that the user should shift in the direction of the green light beam. The apparatus 100 will already have determined that the probe 130 is validly positioned along the intercostal space between the two ribs currently surrounding the matrix array 160, as discussed further below. Conversely, when red, the light indicates that the user should shift in the opposite direction. Alternatively or in addition, the instruction to shift, and the directionality, may appear on the display 110.

The probe may also incorporate an acoustic coupling quality sensor (not shown). Distributed sparsely among the transducer elements 170, i.e., in replacement of individual elements, are pressure sensors 190 devoted to detecting pressure. Detection is interleaved with image acquisition.

When transducer elements 170 in proximity of a pressure sensor 190 are active, and the pressure sensor reading implies lack of pressure, this indicates weak acoustic coupling. More generally, if and when the apparatus 100 decides, based on output of the acoustic coupling quality sensor, that acoustic coupling quality is insufficient, a user alert is issued upon that decision. Visual or auditory user alerts can be provided, via the probe 130 or other parts of the apparatus 100. As an example, the acoustic coupling quality sensor can comprise merely 8 pressure sensors 190 that are disposed among 10,000 transducer elements 170.

Figure 2A:
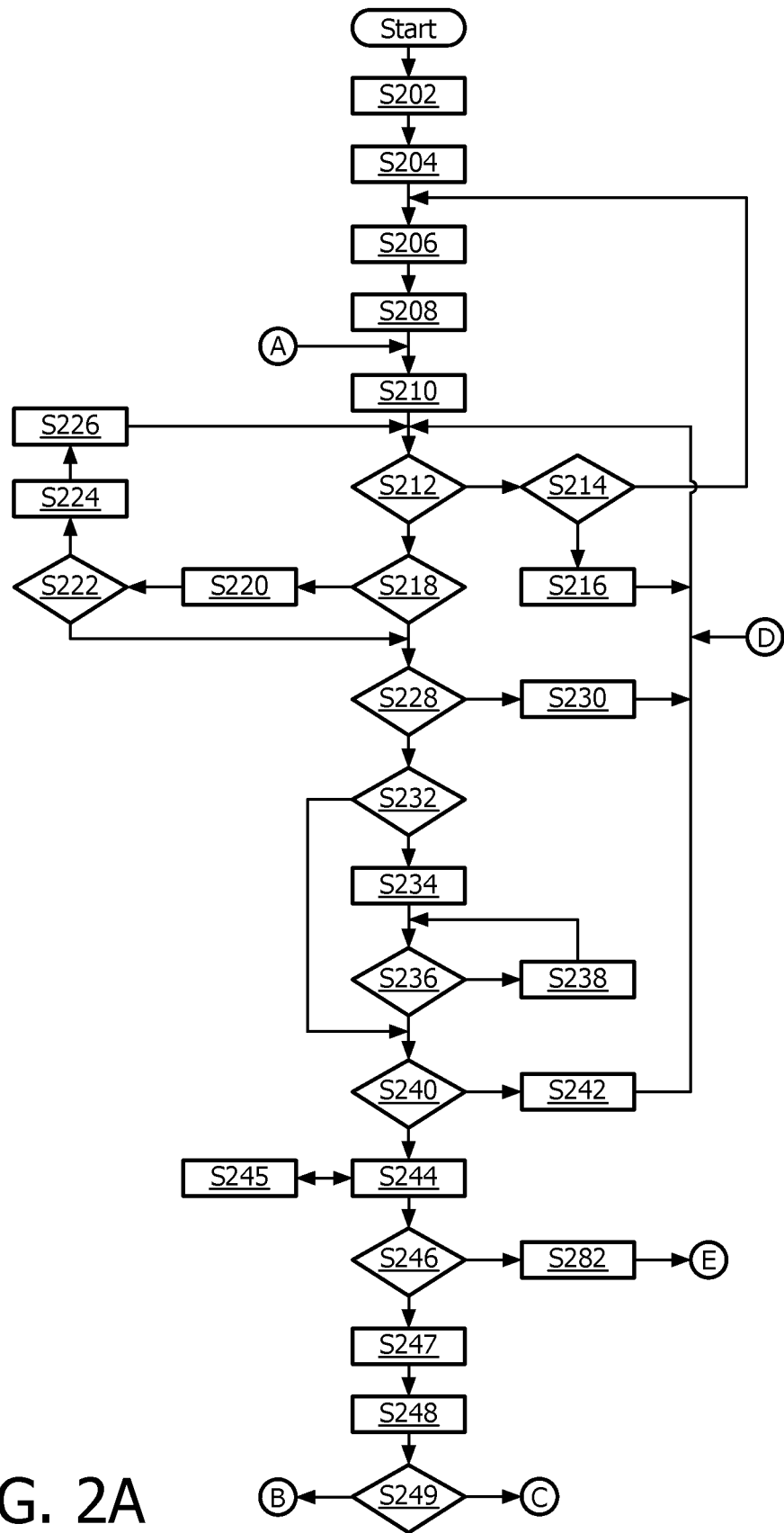
FIGS. 2A and 2B are flow charts of an exemplary ultrasound clinical procedure in accordance with the present invention.
Figure 2B:
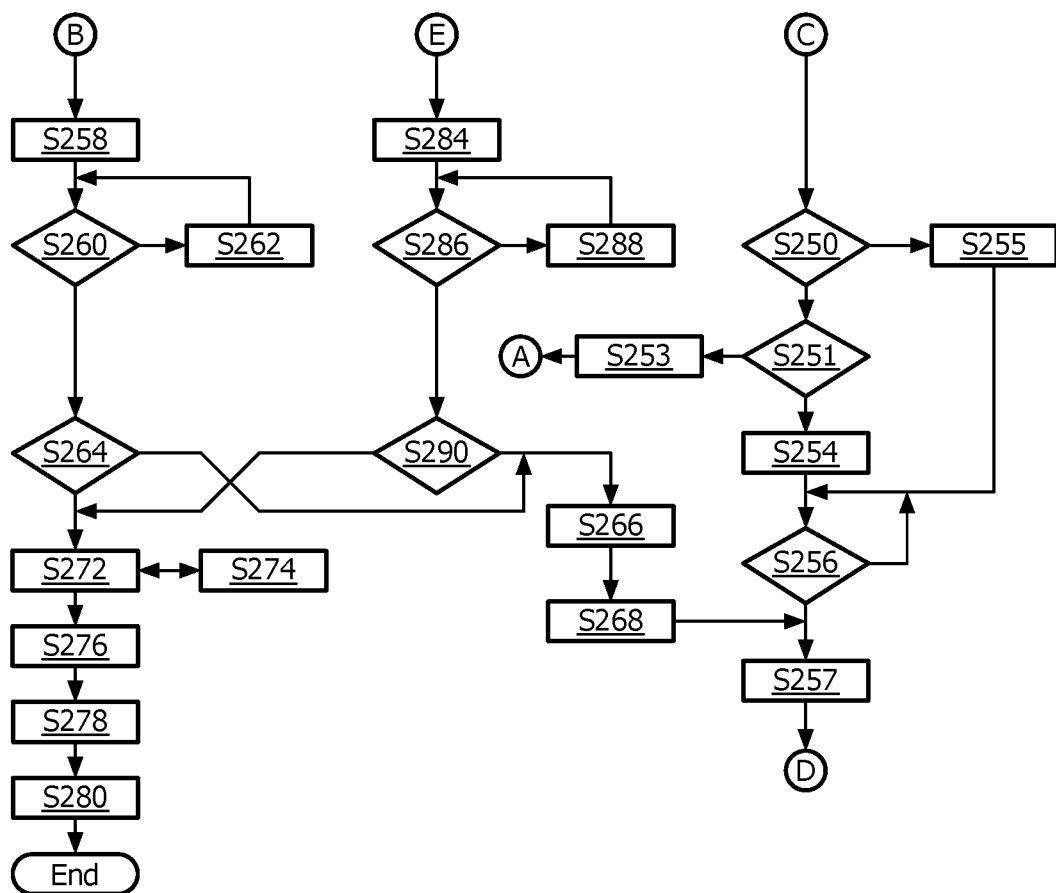

FIGS. 2A and 2B depict, by way of illustrative and non-limitative example, a clinical ultrasound procedure 200 demonstrating how the apparatus 100 visually guides a nurse, or other user, unskilled in sonography. In this embodiment, a four-chamber apical view of the heart for imaging is to be recorded and volumetric cardiac measurements are to be taken and stored. The process is in two stages. In the first stage, the user moves the probe 130 until the imaging detects at least part of the heart, or other organ of interest. In the second stage, the user moves the probe 130, pausing frequently and receiving further instructions shortly after each pause. Sometimes, the apparatus 100 determines that a transition is to be made, from the second stage, back to the first stage. Successful completion of the ultrasound procedure 200 occurs during, i.e., at the end of, the second stage.

Operationally, first, the nurse places the electrocardiogram (ECG) leads on the patient or ultrasound subject, human or animal (step S202). The ECG will serve as part of the cardiac checkup. It also facilitates analysis of the live cardiac imaging that will be recorded. At the outset, the user is instructed generally about the imaging that is to be done, that instructions will be visible on the display 110 and via the lights 180, to stop movement of the probe 130 promptly when instructed, and, when instructed to move the probe, to pause frequently so that the system can take readings (step S204). Also, a stage two flag is cleared as part of the initialization, since the user is initially in stage one of the procedure 200. The user is then instructed to have the patient lie on his or her left side, so that the heart will fall forward in the patient's chest for easier imaging (step S206). The user is instructed to start from the bottom of the rib cage at a point below the left nipple, and to count up to between the fourth and fifth ribs from the bottom of the rib cage (step S208) for a point at which to place the head 150 of the probe 130 for an initial acoustic window. Image acquisition by the probe is live and continuous. The instructions also mention that the probe should be tilted upward to point toward the base of the patient's neck as a first estimate. The instruction now is to: remembering the placement, lift away the probe 130; apply coupling gel around the probe face covering the matrix array 160; and reassume the probe placement as to location, and as to orientation (step S210). If, by a blockage-identification algorithm discussed further below, no ribs are detected (steps S212, S214), a branch back is taken to step S206. Otherwise, if only one rib is detected (step S214), the user is instructed to shift up or down slightly to get between the two ribs (step S216). On-screen, a graphic depiction can be displayed of a probe aimed at one rib being shifted up/down to placement between two ribs. Processing returns to step S212. In this processing loop, and all processing loops that involve issuing a user instruction, the instruction is not listed again if already shown on-screen. If, on the other hand, both ribs are detected, then this aspect of correct probe placement is validated. Query is made as to whether a lung is blocking the current field of view of the probe 130 (step S218). This determination is made by a blockage-identification algorithm discussed further below. If lung tissue is in the field of view (step S218), the user is instructed to have the patient exhale and hold his or her breath (step S220). This might take the lung out of the field of view, since the lung may venture in and out of the field of view with each breath and expiration by the patient. If the lung is detected again and therefore is still blocking the field of view (step S222), the user is instructed to have the patient resume normal breathing (step S224). Since the lung blocking the heart would be the left lung and since the lung is less central on the chest than is the heart, the user is instructed to shift the probe 130 upward, i.e., toward the breastbone (step S226). The pause/go indicator lights 180 on the probe 130 will be green. The user may also be told to tilt the probe 130 slightly to aim more to the left side of the patient, as the probe is shifted up. Return is made to step S212. Alternatively or in addition, the user may be shown an on-screen inverted "V" display by which the user can interactively shift and tilt the probe 130 to avoid the lung. The same "V" display could be used to guide the user to tilt and translate the probe to avoid the ribs. If, on the other hand, after having the patient hold his or her breath (step S220), the lungs are no longer blocking the field of view (step S222), or if the lungs were not initially blocking (step S218), query is made as to whether at least part of the heart is detected in the live imaging by the probe 130 (S228). The Schramm GHT, mentioned above, is utilized for this detecting. Although the left ventricle (LV) may be the part of the heart for which quantification is desired, detecting part of the heart can even involve detecting merely the left atrium, or the mitral valve, for example. A predetermined confidence level must be met in deciding whether the detection has occurred. For example, in the Schramm reference the measure of optimality in determining the set of transformation parameters can be required to meet a predetermined threshold.

If the heart is not detected (S228), the user is instructed to "Shift slowly down away from the breastbone, shift slowly up toward the breastbone, each time to a greater extent." A graphic moving depiction of the pattern may be displayed on the display 110 (step S230). The procedure 200 branches back to step S212.

If, on the other hand, part of the heart is detected (step S228), query is made as to whether the stage two flag, which was cleared during initialization in step S204, is set (step S232). If it is not set (step S232), the user is instructed to pause and wait for instructions (step S234). The pause is needed, because segmentation, even coarse segmentation, requires a short time period, e.g., two seconds. Specifically, the pause/go indicator lights 180 on the probe 130 will turn red and/or the display 110 will show, in red, an instruction to pause. A short audio beep may also issue. The apparatus 100 detects, via the accelerometers in the probe 130, whether motion of the probe has paused (step S236). Until the movement pauses (step S236), the visual and audio feedback to pause is maintained (step S238). When a pause is detected (step S236), a check is again made as to whether part of the heart is detected (step S240). This precaution is taken to determine whether the user has paused quickly enough to still be imaging part of the heart.

If there no longer exists detection of part of the heart (step S240), the instruction (step S242) is "Slowly backtrack your most recent movement and pause when instructed to regain (partial) view of the heart . . . otherwise shift as instructed." Return is then made to step S212.

On the other hand, if at least part of the heart is still detected (step S240), a coarse image-segmentation of the bodily organ, here the heart, is performed (step S244) using a model (step S245).

Provided that the apparatus 100 has electronic steering capability, query is now made as to whether the entire heart, judging from the segment(s), is within the current field of view of the probe 130 (step S246).

If the entire heart is not within the current field of view (step S246) or if the apparatus 100 lacks an electronic steering capability, a coordinate system transformation is computed (step S247). In particular, the segmenting produces one or more segments of the heart having a location and orientation in the image space of the probe 130. The location and orientation are known from the model. Based on the location and orientation, it is determined what would be an optimal viewpoint and viewing orientation for a geometrically-fixed field of view of the probe that covers the entire heart or heart section, e.g., the left ventricle, being investigated. For example, both the mitral valve and the apex of the heart can be identified by segmentation, and an axis connecting them may be, or may be close to, an optimal viewing orientation for quantification and diagnostic cardiac images. The field of view is geometrically fixed, because it is assumed that the user is untrained in sonography and, for simplicity, is being guided merely to move the probe according to visual instructions. The derived optimal viewpoint and viewing orientation will, in general, differ from the current viewpoint and current orientation of the probe. The viewpoints and viewing orientations are all in the image space of the probe 130. The apparatus 100 computes a coordinate system transformation that would bring the current viewpoint and orientation into coincidence with the derived optimal viewpoint and orientation.

After the transformation is computed, the on-screen overall progress bar 178 is updated (step S248).

The progress is based on the magnitude of the translation component of the transformation and, to a lesser degree or at a later stage, on the magnitude of the rotation component of the transformation.

The length of the progress bar 177 could therefore be, percentage-wise, 100 minus a weighted average of the two components that is non-negative and less than unity.

The same or a similar metric is used by the apparatus 100 to decide whether the current view is sufficiently on target for commencing quantification and optionally live imaging acquisition for storage. Alternatively or in addition, the apparatus 100 can determine, based on the model, whether the heart, or heart section, is entirely or sufficiently within the current field of view of the probe 130 (step S249).

If it is determined in step S249 that the current field of view of the probe 130 is not sufficiently close to the optimal field of view, a decision is made as to whether tilting or shifting predominates as the selection for the next user instruction (step S250). Generally, shifting will predominate if any remains; although, if the remainder is small enough, tilting may be sufficient. The parameters for making the decision can be empirically established. Going forward from this part of the procedure 200, presentation to the user of the visual feedback 144 is dynamically arranged selectively based on a comparison between the current field of view of the probe 130 and the derived optimal viewpoint and viewing orientation from step S247. For example, it is based on the need for shifting and/or tilting, those needs being assessed based on the comparison. The selecting inherently occurs according to which of the user instructions mentioned below issues in the procedure 200. It is noted here that the arranging of the presentation of visual feedback 144 earlier in the procedure 200, such as in the steps S212-S228, is done dynamically and selectively and is based on image content acquired but not on the above-mentioned comparison. Therefore, some but not all of the dynamic, selective arranging of visual feedback 144 within the procedure 200 is based on the comparison.

If shifting predominates (step S250), query is made as to whether the translation indicated would involve crossing a rib to enter an adjoining intercostal space, given the position of the ribs (step S251). The apparatus 100 is aware of the position of the ribs through a blockage-identification algorithm mentioned above in relation to steps S212 and S214 and discussed further herein below. If the translation is not feasible (step S251), the user is accordingly instructed to, after re-applying coupling gel to the probe 130, move up, or down, the ribcage (step S253). The stage two flag is cleared, and processing returns to step S210. If, on the other hand, the translation is feasible (step S251), the user is instructed to shift slowly in the direction determined by the apparatus 100, pausing frequently (step S254). Thus, this user instruction is among those dynamically and selectively arranged based on the above-mentioned comparison.

If, on the other hand, shifting does not predominate in step S250, the user is instructed to tilt the probe 130 slowly in the determined direction (step S255). The instruction may be "tilt slowly aiming inward toward the breastbone, stopping frequently" or "tilt slowly aiming downward toward the patient's feet, stopping frequently", some combination of these two instructions, etc. This instruction then is among those dynamically and selectively arranged based on the above-mentioned comparison.

Alternatively or in addition, the display 110 may show an interactive graphical depiction of the segmented organ, here segments defining a heart, as a segmented on-screen object with a superimposed, inverted "V" representing the field of view of the probe 130. A second, separate, concurrent depiction may be shown for a "V" in the orthogonal direction. This graphical depiction is discussed further below.

After the instruction for either step S254 or S255 issues, query is made as to whether movement since step S236 has occurred. This can be determined via the accelerometers in the probe 130. If such movement has occurred and if there is no movement now (step S256), the stage two flag is set (step S257), and processing returns to step S212.

If, on the other hand, it is determined in step S249 that the current field of view of the probe 130 is sufficiently close to the optimal field of view, the apparatus 100 issues an instruction to halt (step S258). Specifically, the pause/go indicator lights 180 on the probe 130 will turn red and/or the display 110 will show, in red, an instruction to halt. A short audio beep may also issue. The apparatus 100 detects, via the accelerometers in the probe 130, whether motion of the probe has halted, i.e., paused or terminated (step S260). Until the movement halts (step S260), the visual and audio feedback to halt is maintained (step S262). Once the movement halts (step S260), query is made, as in step S249, as to whether the current view is sufficiently on target for commencing quantification and optionally live imaging acquisition for storage (step S264). If the current view is not, i.e., is no longer, on target (step S264), the progress bar 178 is accordingly shortened to reflect the setback in progress toward completion of the procedure 200 (step S266). An instruction issues for the user to slowly backtrack the most recent probe movement, stopping frequently (step S268). Processing branches to step S257. If, on the other hand, the current view is sufficiently on target for commencing quantification and optionally live imaging acquisition for storage (step S264), the user is notified to hold the probe still for completion of the procedure 200 (step S270). Fine segmentation is performed for quantification (step S272). The model is utilized for this purpose (step S274). The apparatus 100 starts recording live imaging of the heart or heart section (step S276). If the apparatus 100 includes an electronic steering capability, various views of the heart such as the standard views can be played back from the recording. The apparatus also and makes volumetric measurements from the segmentation (step S278). For example, left ventricle (LV) size is computed, over a heart cycle, by finding the average or maximum length and finding the average or maximum breadth, for example. Likewise, ejection fraction is computed by detecting, over a cardiac cycle, maximum and minimum LV volume, and taking a ratio of the two quantities. The quantification data is stored in memory (step S280).

If, on the other hand, the entire heart is within the current field of view (step S246) and if the apparatus 100 has an electronic steering capability, the progress bar 177 is made to reflect near completion (step S282). An instruction to halt is given in step S284. While movement of the probe 130 is detected (step S286), a user alert to halt is maintained (step S288). Once it is detected that the probe 130 is halted (step S286), query is again made as to whether the entire heart is in the field of view (step S290). If the entire heart is still in the field of view (step S290), processing branches to step S270 to instruct the user to pause for completion of the procedure 200. Otherwise, if the entire heart is no longer within the field of view (step S290), processing branches to step S266 to try to recover the image of the entire heart.

Figure 3:
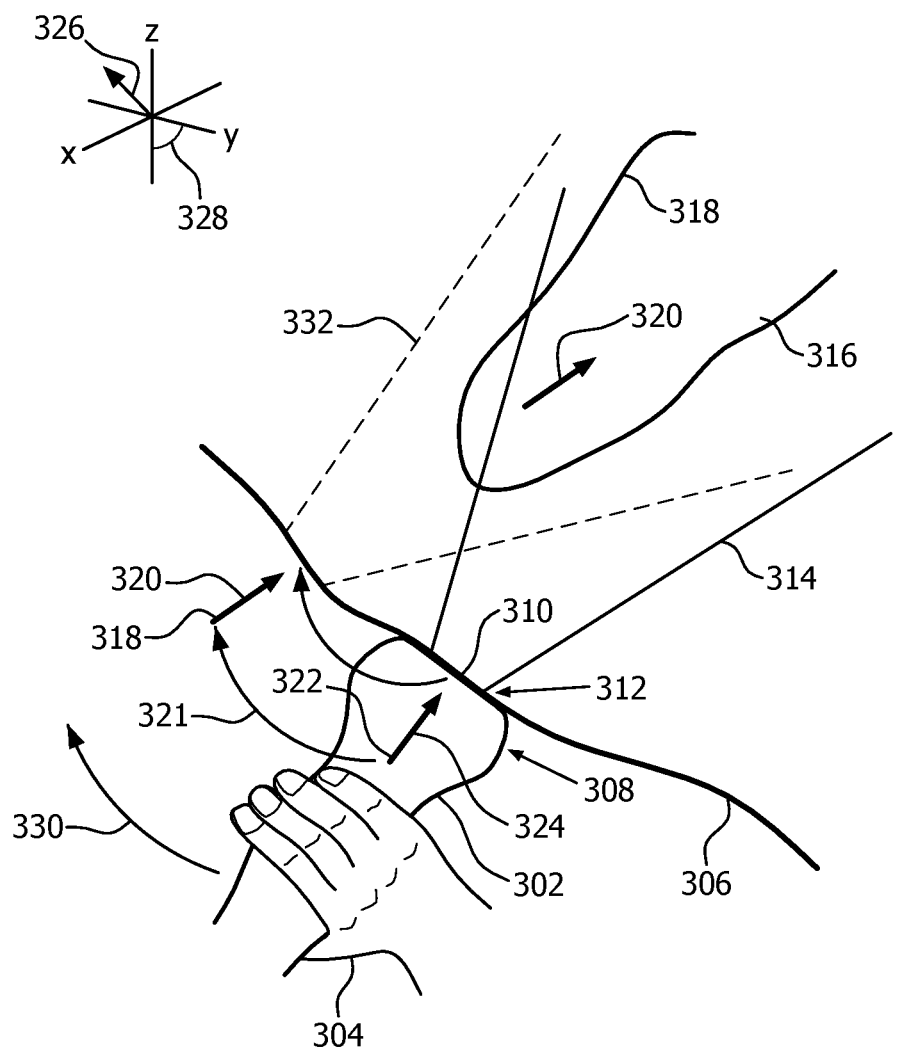
FIG. 3 is a conceptual diagram of how the apparatus is able to guide, in real time, the placement of the acoustic window.

FIG. 3 depicts, conceptually, how the apparatus 100 is able to guide, in real time, placement of the acoustic window. A probe 302 is held by the clinician's hand 304 against the skin 306 of a patient. More specifically, the probe 302 has a head 308 which has a face 310 for placement against the skin 306, separated from the skin only by the acoustic coupling medium such as a specialized gel. Within the head 308 and along the face 310 is a matrix array 312. Extending from the matrix array 312 is a field of view 314. The heart 316 of the patient is partially, here mostly,within the field of view 314, and is being imaged via the probe 302. Since part of the heart 316 is detected with a sufficient level of confidence, the clinician has been instructed to pause and has done so promptly. As a result of image segmentation into segments 318, the apparatus 100 determines, via the model, an orientation 320 that would provide an optimal, or targeted, view of the heart 316 if the probe 302, or some part of the probe such as the matrix array 312, were to assume that orientation from an appropriate location 318. The model also provides the location 318. For simplicity of explanation, a curved arrow 321 in FIG. 3 starts at a location 322 and orientation 324 of the probe 302. It ends at the model-provided location 318 and model-provided orientation 320 that are derived from the image segmentation. The curved arrow 321 represents comparison of the field of view 314 with the model-provided location and orientation 318, 320. The comparison involves a coordinate system transformation that would bring the model-provided location and orientation 318, 320 into coincidence with the current location 322 and current orientation 324 of the probe 302. The transformation has a translational component 326 and a rotational component 328. Visual feedback 144 in the procedure 200 is selected based on magnitudes of the components 326, 328, as for example in steps S248, S249 and S264 of FIGS. 2A and 2B. Another curved arrow 330 in FIG. 3 shows the clinician's hand 304 maneuvering the probe 302, based on the feedback 144, into an apical view 332.

In the depicted example, the heart 316 is partially outside the current field of view 314. Electronic steering into a favorable field of view corresponding to the apical view 332 still fails to capture imaging content that was out of view prior to the electronic steering. Accordingly, relying on electronic steering in the depicted example to shorten the procedure 200 might compromise the result, depending upon the impact of losing that particular image content.

If, however, FIG. 3 were to be redrawn with the heart 316 completely within the current field of view 314, electronic steering proceeds as described above, provided that the apparatus 100 has an electronic steering capability. Thus, the apical view 332 is achieved without maneuvering the probe 302, that maneuvering being represented by the curved arrow 330. Instead, it is achieved by electronic steering. Although the manual maneuvering of the probe 203 may have been needed earlier in the procedure to achieve detection of part of the heart 316 (step S228), electronic steering can, once the entire heart is in view, alleviate the need for further manual maneuvering of the probe.

Advantageously, the user is guided throughout a procedure for achieving an apical view of the heart.

As mentioned herein above, detecting that the ribs bordering the current intercostal space are within the field of view is part of the validation that the current acoustic window, placed in finding an optimal acoustic window, is valid. User instructions on how to maneuver the probe around the lungs to view the heart are also mentioned herein above.

Echocardiography is challenging as the heart is surrounded by ribs and lung tissue. Ultrasound can hardly penetrate calcified ribs (typically encountered in the apical view) and lung tissue because of severe acoustic impedance mismatch between them and other soft tissues. In addition, ultrasound absorption in ribs is quite high compared to tissue. Conventionally, optimization of ultrasound image quality is done solely by the user based on real-time-displayed grayscale ultrasound images on the screen. Though experienced users are usually capable of recognizing image degradation and improving image quality accordingly by moving the probe to a better position, less experienced users might acquire compromised images because of inferior hand-eye coordination and less awareness of artifacts. Successful ultrasound scanning strongly relies on training and experience of the user. To help inexperienced or less experienced users acquire meaningful information from the heart using echocardiography, an anatomically intelligent ultrasound system is desired.

Since ultrasound can hardly penetrate a calcified rib, deep echoes of an ultrasound beam hitting a calcified rib are very unlikely to be from tissues under the rib. Rather, they might be picked up by sidelobes. The visual artifact is recognizable by an experience sonographer viewing the (grayscale) sonogram, but can easily be unrecognized by the inexperienced user.

Also, to get good image quality for an inexperienced user, an ultrasound system should be aware of the presence of lung tissue.

One blockage-identification algorithm described below is specialized for detecting lung tissue, and especially rib tissue, blocking the field of view. A second blockage-identification algorithm described below is tailored especially for detecting lung tissue blockage. They are discussed in view of the following drawings.

Figure 4A:
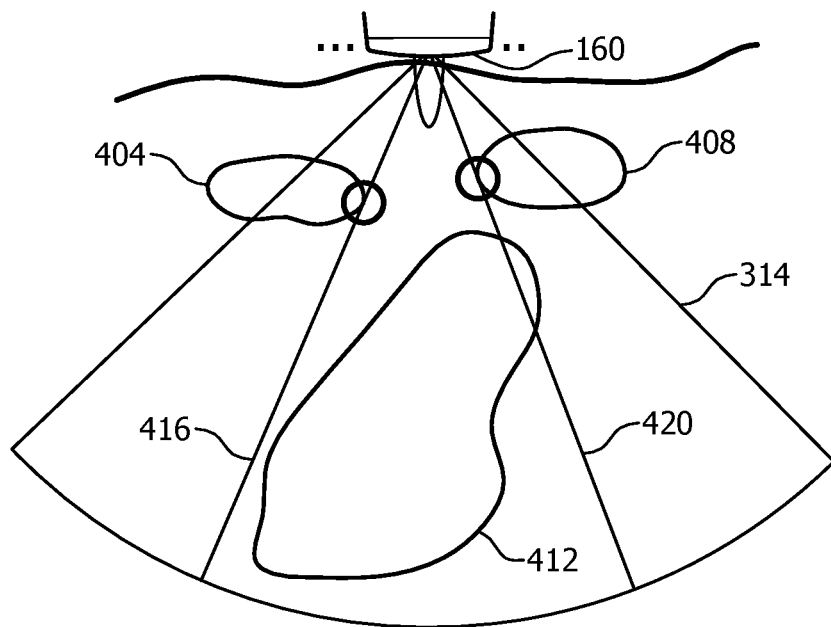
FIGS. 4A and 4B are diagrams showing examples of schemes for imaging-blockage avoidance that use on-screen guidance images of segments disposed with respect to a field of view of an ultrasonic probe, in accordance with the present invention.
Figure 4B:
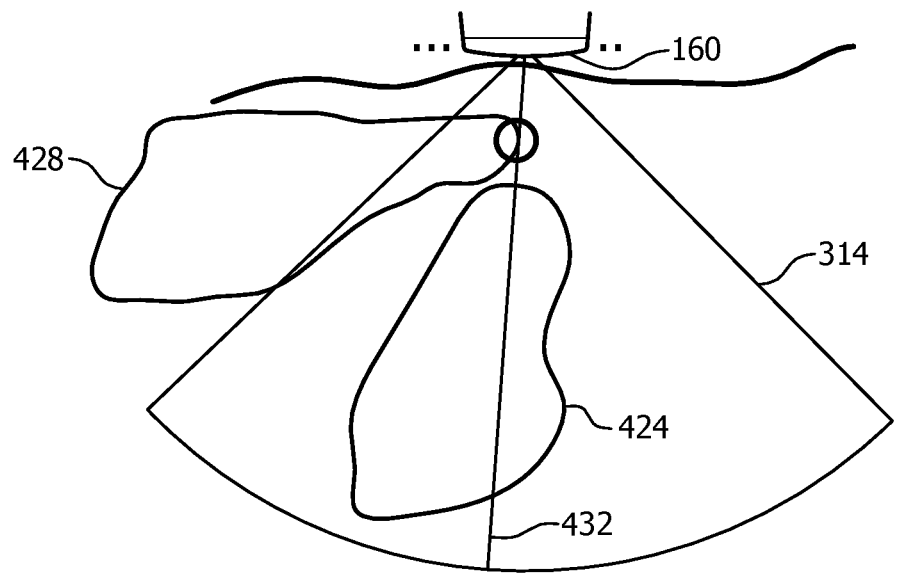

FIGS. 4A and 4B show examples of schemes for imaging-blockage avoidance that use on-screen guidance images of segments disposed with respect to a field of view of an ultrasonic probe.

Both figures feature a sonogram. The FIG. 4A sonogram is an image slice that runs along the length of a patient; whereas, the FIG. 4B sonogram is an image slice that runs along the width of a patient.

FIG. 4A relates not only to the first algorithm, but also to an interactive display as part of the visual feedback 144.

The matrix array 160 has a current field of view 314 that partially includes ribs 404, 408 and partially (and here almost entirely) includes a heart 412. The first algorithm calculates blockage boundary lines 416, 420 that correspond to the boundary between good ultrasound beams and ones that are bad due to blockage by the ribs 404, 408.

Coherence of channel data is used to detect blockage. Each channel delivers its respective radiofrequency data magnitude associated with its respective fixed transducer element 170 or patch of elements. As ultrasound echoes return, their incident pressures on the elements 170 are sampled quickly and periodically. The samples are delayed with respect to each other according to the line-of-sight travel time geometry of the field point being evaluated. Here, "coherence" means similarity among data recorded by different channels of an array after applying the above-mentioned receiving focusing delays.

One gauge of coherence is a beamsummed-data-based coherence estimation method, such as the one described in U.S. Patent Publication No. 2009/0141957 to Yen et al., the entire disclosure of which is incorporated herein by reference.

Figure 5:
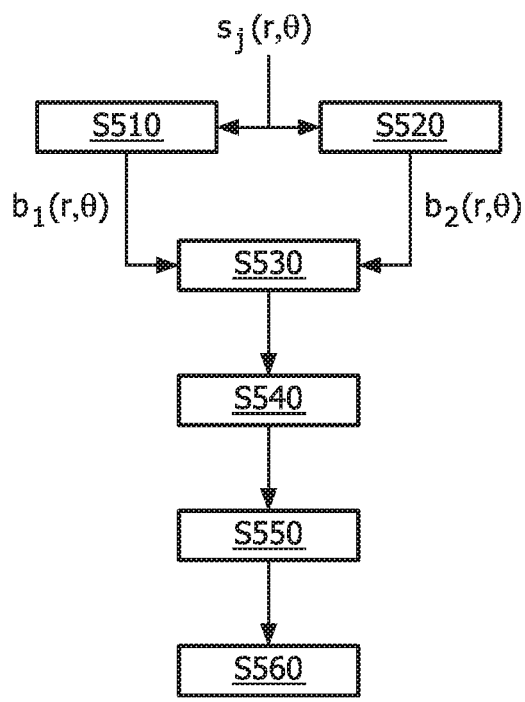
FIG. 5 is a flow chart, and formula list, relating to FIG. 4A.

The estimation method can be tailored to detecting rib and lung blockage, and is demonstrated below using two beamformers. Let $s_j(r,\theta)$ denote the (real-valued) channel data at depth r received by the j-th channel after applying the focusing delay, and let $C_1$ and $C_2$ denote the set of channels used in the first and the second beamformer, respectively. The output of the k-th (k=1, 2) beamformer is $b_k(r,\theta)$, the formula for which is shown in FIG. 5. When all the channel data $s_j(r,\theta)$ are identical across channels, $b_1(r,\theta)$ and $b_2(r,\theta)$ will be highly correlated no matter how $C_1$ and $C_2$ are chosen. On the other hand, when the channel data are mainly contributed by scatterers in sidelobe regions, the correlation between $b_1$ and $b_2$ can drop significantly if $C_1$ and $C_2$ are properly chosen. $C_1$ and $C_2$ can be complementary, interleaving apertures. In short, it is possible to distinguish between on-axis signals and off-axis signals based on correlation between $b_1$ and $b_2$. The output of the correlator is the correlation coefficient $\rho(r,\theta)$ of $b_1(r,\theta)$ and $b_2(r,\theta)$ defined as listed in FIG. 5, where w is a real symmetric weighting function. $\rho(r,\theta)$ is then lowpass filtered to get a smoothed correlation map $\hat{\rho}(r,\theta)$ which is used for blockage detection. A flow diagram for the algorithm, i.e., the "first algorithm", is shown in FIG. 5. Sums of $s_j(r,\theta)$ are taken for $C_1$ (step S510) and for $C_2$ (step S520). They are correlated to calculate the correlation coefficient $\rho(r,\theta)$ (step S530) which is low-pass filtered (step S540) to produce the smoothed correlation map $\hat{\rho}(r,\theta)$ used for blockage detection (step S550). The edge lines are then generated for the inverted "V" display (step S560).

In a specific example, the data is acquired at 32 MHz sampling rate in a pulse-inversion mode using a probe having 80 elements 170. Each frame has 44 beams and the beam density is 0.4944 beam/degree. The center frequency is 1.3 and 2.6 MHz on transmit and on receive, respectively. $C_1$={20-22, 26-28, 32-34, 38-40, 44-46, 50-52, 56-58} and $C_2=\{23\text{-}25, 29\text{-}31, 35\text{-}37, 41\text{-}43, 47\text{-}49, 53\text{-}55, 59\text{-}61\}$. The weighting function w used in the correlator is a 51 (axially or in the r direction) by 1 (laterally or in the θ direction) boxcar and the smoothing filter is a 501 by 3 boxcar. Due to the periodic structure of the apertures, sensitivity of the correlation coefficient ρ to off-axis signals varies periodically with the direction of off-axis signals. This periodicity can be alleviated by randomizing sub-aperture sizes while still keeping both apertures complementary.

To verify whether a beam is blocked, a count is made of the number of points with a correlation coefficient ($\hat{\rho}$) higher than 0.55 between 72 and 180 mm in depth. If at least 400 points (at 32 MHz sampling rate) in a beam have high coherence, this beam is considered penetrating into tissue. Otherwise it is considered blocked by a rib.

Referring back to FIG. 4A, and counting the 80 channels from left to right, perhaps the $20^{th}$ channel has the first beam exhibiting high coherence; whereas, the $19^{th}$ beam does not exhibit high coherence. Thus, the first blockage boundary line 416 is shown in FIG. 4A at the $19^{th}$ beam. Likewise, if the $59^{th}$ channel exhibits high coherence, but the $60^{th}$ channel does not exhibit high coherence, the second blockage boundary line 420 is placed in coincidence with the $59^{th}$ beam.

The upper bound of the depth range is not critical. 72 mm, much larger than the depth of human ribs in general, can be chosen as the lower bound because high coherence factor values might be present in regions right below a rib due to multiple reflections (or reverberation) and such reflections tend to fade away with depth.

The apertures described do not include channels in both ends of the full aperture. Though apertures can be extended to include those channels, the number of blocked beams might be underestimated if large apertures are used. This is because the correlation coefficient of complementary aperture outputs could still be high if part of the large complementary apertures is not blocked.

Though the embodiment above uses 2D images acquired with a 1D probe, the methodology can be applied to matrix probes and therefore 3D volumetric imaging to guide novice users to perform volumetric acquisitions.

FIG. 4A also depicts an image that can be displayed for interactively guiding the clinician. The image of the heart 412 can be implemented as the segment(s) defining the heart by virtue of the coarse segmentation (step S244). The heart 412 is barely but partially outside the field of view 314. As the clinician shifts the probe 302 according to visual feedback 144 on-screen or in the form a green light 180 on the probe, the FIG. 4A image updates in real time. The inverted "V" can easily be made to fully encompass the desired organ, here a heart. A FIG. 4A image, as part of the visual feedback 144, may supplement steps S212, S214 and S255 described above in connection with FIGS. 2A and 2B.

To optimize probe positioning, the span of V's can be enlarged through the use of an x-plane display.

Analogous to FIG. 4A, FIG. 4B relates not only to the second algorithm, but also to an interactive display as part of the visual feedback 144.

The matrix array 160 has a current field of view 314 that includes a heart 424 and part of a lung 428. The second algorithm calculates a blockage boundary line 432 that corresponds to the boundary between good ultrasound beams and ones that are bad due to blockage by the lung 428.

In the second algorithm, the center frequency of radiofrequency (RF) data acquired in pulse inversion (PI) modes is used as the parameter to distinguish lung tissue from heart tissue.

Figure 6A:
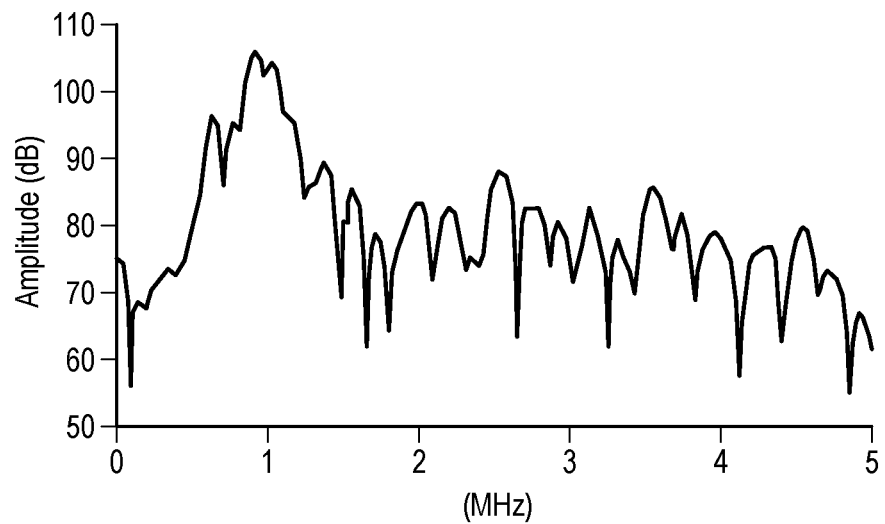
FIGS. 6A, 6B and 6C are, respectively, exemplary graphs of radiofrequency data used to distinguish lung tissue from heart tissue, and an algorithm used in the distinguishing, in accordance with the present invention.
Figure 6B:
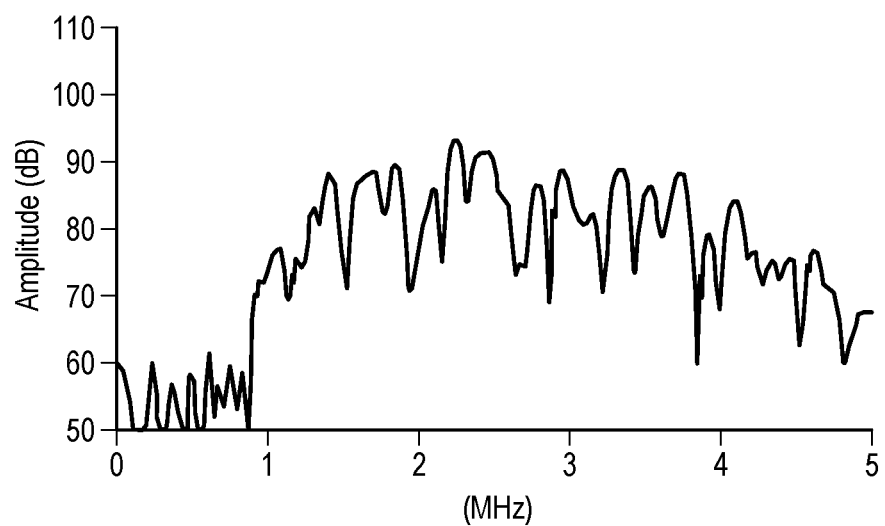

Sample radiofrequency data with a transmit center frequency of 2.1 MHz is shown in FIGS. 6A and 6B. The FIG. 6A graph represents the interrogation of lung tissue; whereas, the FIG. 6B graph represents the interrogation of heart tissue. Lung and heart tissue look more different in pulse inversion imaging that in conventional imaging. For example, lung tissue responded better to lower frequencies.

The FIG. 6A graph resulted from linear response of the lung tissue to self-demodulated signals. With wideband transmission, after nonlinear propagation the summation of the positive and the negative pulse will present a finite signal around 1 MHz, roughly half of the center frequency on transmit, a phenomenon called self-demodulation. Lung tissue responds to this low-frequency signal better than heart tissue. On the other hand, compared to lung tissue, heart tissue tends to favor higher frequency components in a PI mode because its stronger motion results in less perfect cancellation at higher frequencies.

Part of the second algorithm involves estimating the center frequency of the RF data. Let r(n) be a sampled A-line signal and R (n) be its complex envelope. $f_c(n)$, the local center frequency of r(n), is related to R (n) by $$\arg\{R(n+1)R^*(n)\} \cong \frac{\arg\{R(n+1)R^*(n-1)\}}{2} \cong \frac{2\pi f_c(n)}{f_s}, \quad (1)$$

where arg{.} denotes phase/argument and A is the sampling rate. Estimators of $f_c(n)$ can be derived based on (1). An example of an estimator is:

$$\hat{f}_c(n) \equiv \frac{\arg\left\{\sum_{i=-m}^{i=m} w(i)R(n+i+1)R^*(n+i-1)\right\}}{4\pi} f_s \quad (2)$$

as the estimator. Averaging based on the window function w(i) reduces variance.

In one example, transmitting is at 2.1 MHz in a high resolution mode, the sampling rate is 32 MHz and the beam density is 0.72 beam/degree. One image or frame consists of 64 beams with 2 transmits per beam. The RF echoes in a frame are denoted as $\{r_p(n,\theta), r_n(n,\theta)\}$, where the subscripts p and n stand for positive and negative pulse on transmit respectively, and n and θ=θ(k) (k is the beam index) denote time index and angle respectively.

Figure 6C:
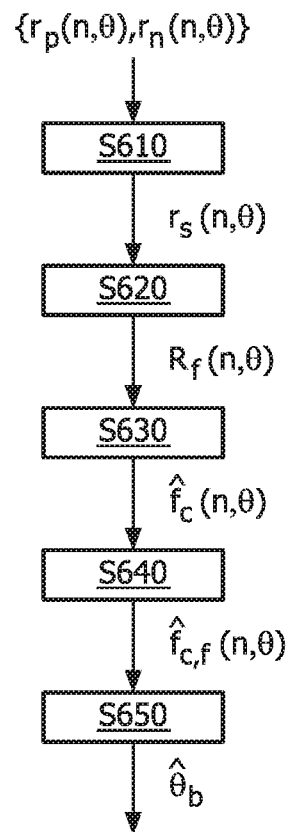

FIG. 6C shows the flow diagram of first version of the second algorithm, where $r_s(n,\theta) \equiv r_p(n,\theta) + r_n(n,\theta)$, $R_f(n,\theta) = r_s(n,\theta) \otimes h(n)$, $\otimes$ denotes convolution, and h(n) is a 121-tap single-sided complex bandpass filter between 0.95 and 2.05 MHz. The center frequency map $\hat{f}_c(n,\theta)$ is obtained beam by beam based on equation (2) with a 301-tap Hamming window, and then smoothed by a 301 (axially or in the n direction) by 5 (laterally or in the θ direction) boxcar filter to get $\hat{f}_{c,f}(n,\theta)$. The last step is to estimate the boundary angle between heart and lung using the smoothed center frequency map $\hat{f}_{c,f}(n,\theta)$. The steps in FIG. 6C are summation (step S610), complex temporal filtering (step S620), center frequency estimation (step S630), 2D filtering (step S640) and boundary estimation (step S650).

Estimation of the boundary angle involves multiple thresholding. Starting with the first thresholding relation: For a beam (i.e., give a θ) to qualify as a heart region, the center frequency has to satisfy the following condition:

$$\frac{1}{1501}\sum_{m=0}^{1500}\hat{f}_{c,f}(n+m,\ \theta) \geq f_{u1} \text{ for all } n \in [1500, 2500]. \quad (3)$$

That is, only if the average center frequencies between the 1500th and 3000th points (between 36 mm and 72 mm), between the 1501st and 3001st points, . . . , and between the 2500th and 4000th points (between 60 mm and 96 mm) are all no lower than $f_{u1}$, can a beam be considered to be passing through heart tissue. The collection of the index of qualified beams is denoted as the set $A_1$. For example, $A_1=\{3, 4, \ldots, 32\}$ (noting that the 64 beams are counted from right to left in FIG. 4B and that the first two and last two beams do not qualify because of the spatial smoothing filter) for $f_{u1}=1.37$ MHz. Accordingly, the boundary angle can be estimated as the average angle over beams 32 and 33, $\theta(k)$ being an increasing function of k. The blockage boundary line 432 corresponds to the boundary angle.

The lung tissue can never appear on the right side of the heart (from the perspective patient) as long as the probe is correctly positioned, unless the image shown in FIG. 4B is, in effect, flipped. We can therefore always estimate the boundary based on the leftmost beam satisfying the condition defined in (3). For example, if $A_1=\{14,15, \ldots, 32\}$, the boundary angle still could be estimated as the average angle over beams 32 and 33.

Robustness of lung identification can be improved by including additional criteria. The second threshold is used to detect regions with very low center frequency: Given a beam angle $\theta$, if the center frequency satisfies $$\frac{1}{501}\sum_{m=0}^{500}\hat{f}_{c,f}(n+m,\ \theta) < f_1 \text{ for any } n \in [1750, 3750], \quad (4)$$

this beam can be considered passing through lung tissue. The collection of the index of beams satisfying (4) is denoted as $A_2$. $A_2=\{3,4, \ldots, 32\}$ in the case shown in FIG. 4 for $f_1=1.27$ MHz and therefore has no conflict with the corresponding $A_1$.

The third (and the last) threshold is used to detect regions with very high center frequency: Given a beam angle $\theta(k)$, if the center frequency satisfies $$\frac{1}{2001}\sum_{n=2000}^{4000}\hat{f}_{c,f}[n,\ \theta(k+m)] > f_{u2} \text{ for all } m \in \{-2, -1, 0, 1, 2\}, \quad (5)$$

this beam is considered to be passing through heart tissue. That is, if 5 consecutive beams present very high center frequency, the central beam has a high chance of passing heart tissue. The collection of the index of beams satisfying (5) is denoted as $A_3$.

In practice, $A_1$, $A_2$ and $A_3$ might not be consistent with each other. For example, the intersection of $A_1$ and $A_2$ might be nonempty meaning that some beam could be considered passing both heart and lung tissue. Accordingly, the collections may be prioritized. Specifically $A_3$ (the very high frequency condition defined in (5)) is given the highest priority and $A_1$ (the high frequency condition defined in (3)) is given the lowest priority. The "adjusted heart tissue set" is defined as $$A_h = \{k | k \in A_1 \text{ and } k < l \text{ for any } l \in A'_2 \text{ that is larger than } \max(A_3)\}, \quad (6)$$

where $\max(A_3)$ is the maximum element of $A_3$ and is defined as $-\infty$ if $A_3$ is empty. The following is an equivalent definition:

$$A_h = \{5 | k \in A_1 \text{ and } k < l \text{ for any } l \in A'_2\} \quad (7)$$

where $$A'_2 = \{l | l \in A_2 \text{ and } l > j \text{ for any } j \in A_3\} \quad (8)$$

The boundary between heart and lung is estimated based on the largest element of $A_h$. For example, if $A_1=\{5,6, \ldots, 50\}$, $A_2=\{3,4, 49,50,51\}$ and $A_3=\{11,12,13\}$, then $A'_2=\{49,50, 51\}$, $A_h32\ \{5,6, \ldots, 48\}$, and the estimated boundary angle $\hat{\theta}_b$ is the average angle over beams 48 and 49. An empty $A_h$ indicates lung tissue occupying the whole image. If $A_h$ is not empty, $$\hat{\theta}_b \equiv \frac{1}{2}\{\theta[\max(A_h)] + \theta[\max(A_h) + 1]\} = \theta[\max(A_h)] + \frac{1}{2}\Delta\theta, \quad (9)$$

where $\Delta\theta = \theta(k+1) - \theta(k)$. Because the 2D smoothing filter deteriorates beams on the sides, it is concluded that no lung tissue appears in the image if $$\theta[\max(A_h)] \geq \text{(beam number)} -$$
$$\text{(half the lateral dimension of the 2D smoothing filter)} = 64 -$$
$$\frac{5-1}{2} = 62.$$

The role of $f_{u1}$ is much more important than that of $f_1$, but occasionally existence of $A_2$ contributes positively in determining the boundary. To recap, in this first version of the second algorithm, $f_{u1}=1.37$ MHz, $f_1=1.27$ MHz, and $f_{u2}=\infty$.

Figure 7:
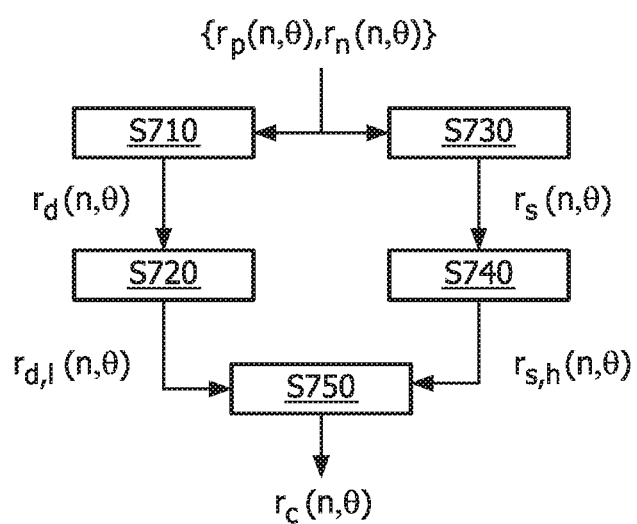
FIG. 7 is a flow chart representative of an exemplary lung identification algorithm based on a one-dimensional probe.

A second version of the second algorithm also pertains to 1D probes and for PI data acquired in high resolution mode. As mentioned above, lung tissue responds to low-frequency signal components well in a linear fashion and motion causes less perfect cancellation at higher frequencies in heart tissue in a PI mode. This implies the possibility of performance improvement by replacing $r_s(n,\theta)$ with a composite signal $r_c(n,\theta)$ in the signal processing chain shown in FIG. 6C. For this reason, there is a second version of the second algorithm. FIG. 7 shows how $r_c(n,\theta)$ is formed, where $r_d(n,\theta) \equiv r_p(n,\theta) - r_n(n,\theta)$ which is step S710, $r_{d,1}(n,\theta) \equiv r_d(n, \theta) \otimes h_l(n)$ which is step S720, step S730 is identical to step S610, $r_{s,h}(n,\theta) \equiv r_s(n,\theta) \otimes h_h(n)$ which is step S740, $r_c(n, \theta) \equiv w_d r_{d,1}(n,\theta) + w_s r_{s,h}(n,\theta)$ which is step S750, $h_l(n)$ is a 101-tap real lowpass filter cutting off at 0.8 MHz, and $h_h(n)$ is a 101-tap real highpass filter cutting off at 1.15 MHz. Echoes from lung tissue favor $r_{d,1}(n,\theta)$ (because it responds to low-frequency components well) and echoes from heart tissue favor $r_{s,h}(n,\theta)$ (because of more motion). $w_d$ and $w_s$ are weights used to balance the two forces. The signal processing following $r_c(n,\theta)$ remains the same as that following $r_s(n,\theta)$ in FIG. 6C. Exemplary parameters are $w_d=1.2$, $w_s=1$, $f_{u1}=1.4$ MHz, $f_1=1.2$ MHz, and $f_{u2}=1.5$ MHz.

A matrix probe version of the second algorithm is based on the second version—composite signals are used for center frequency estimation. RF data can be collected, for example, using penetration imaging mode with PI enabled and a center frequency of 2.2 MHz. Lateral and elevational widths can be maximal.

Each volume has 40 (lateral) by 33 (elevational) A-lines on transmit (with 2 transmit events per A-line due to PI acquisition) and 80 by 66 A-lines on receive sampled at 16 MHz because of the 4× beamformer. The four signals of each transmit direction are summed to get RF echoes $\{r_p(n,\theta,\phi), r_n(n,\theta,\phi)\}$ with 40 θ values and 33 θ values. The lateral beam density is 0.41 beam per degree.

Figure 8:
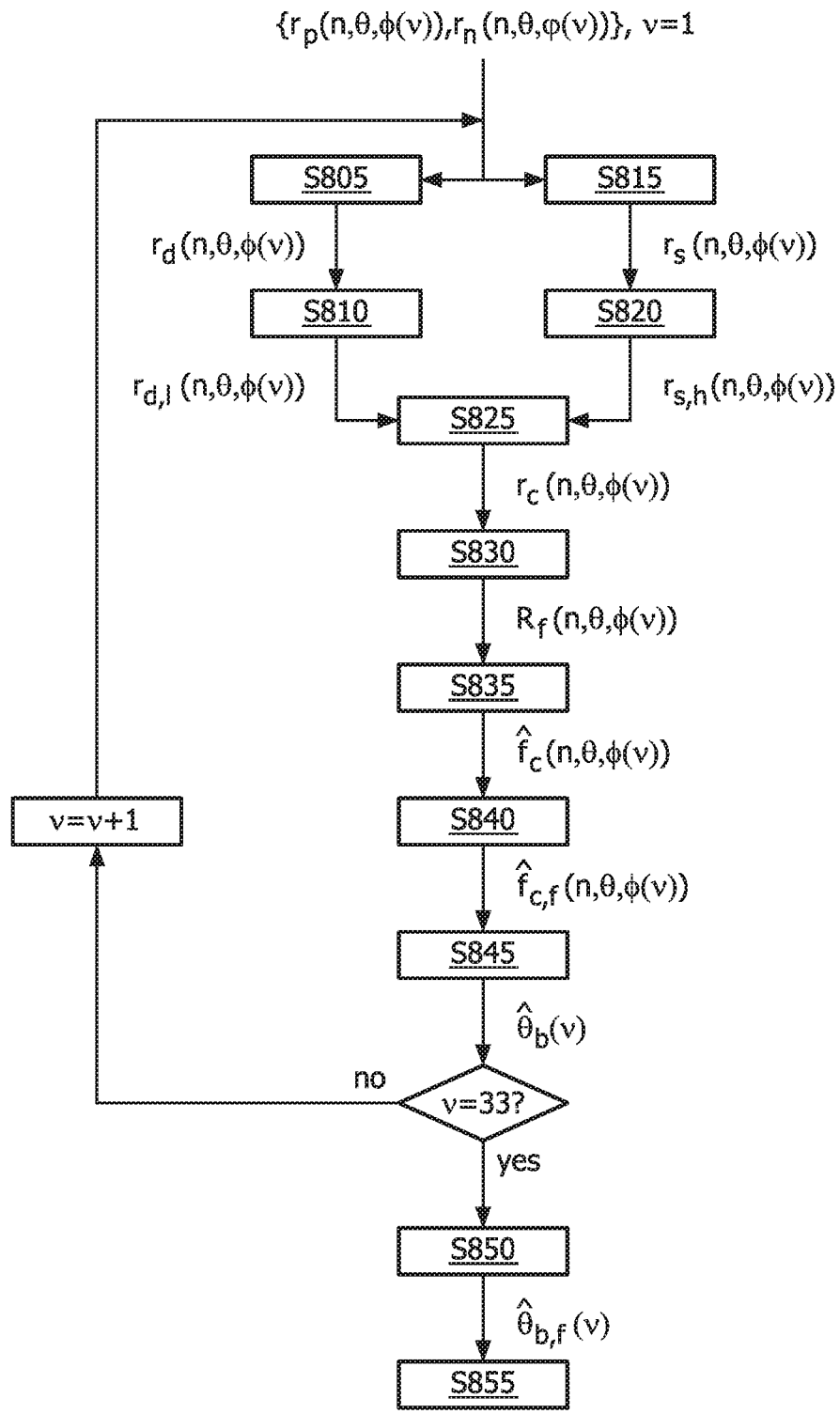
FIG. 8 is a flow chart representative of an exemplary lung identification algorithm based on a matrix probe.

FIG. 8 shows the flow diagram of the matrix probe version of the second algorithm, with the temporal sampling rate at 16 MHz. The steps are: subtraction (step S805), low-pass filtering (step S810), summation (step S815), high-pass filtering (step S820), weighted summation (step S825), complex temporal filtering (step S830), center frequency estimation (step S835), 2D filtering (step S840), boundary estimation (step S845), median filtering (step S850) and visualization across planes (step S855). In short, $\phi=\phi(v)$, $r_d(n,\theta,\phi) \equiv r_p(n,\theta,\phi) - r_n(n,\theta,\phi)$, $r_s(n,\theta,\phi)) r_p(n,\theta,\phi) + r_n(n, (n,\theta, \phi) r_d(n,\theta,\phi) \otimes h_1(n)$, $r_{s,h}(n,\theta,\phi) \equiv r_s(n,\theta,\phi) \otimes h_h(n)$, $r_c(n,\theta,\phi) \equiv w_d r_{d,l}(n,\theta,\phi) + w_s r_{s,h}(n,\theta,\phi)$, $h_1(n)$ is a 51-tap real lowpass filter cutting off at 0.8 MHz, $h_u(n)$ is a 51-tap real highpass filter cutting off at 1.3 MHz, $w_d=2$, and $w_s=1$. The complex envelope $R_f(n,\theta,\phi) \equiv r_c(n,\theta,\phi) \otimes h(n)$, where $h(n)$ is a 61-tap single-sided complex bandpass filter between 0.95 and 2.05 MHz. In each elevational plane, the center frequency map $\hat{f}_c(n,\theta,\phi)$ is obtained beam by beam based on equation (2) with a 151-tap Hamming window, and then smoothed by a 151 (in the n direction) by 3 (in the θ direction) boxcar filter to get $\hat{f}_{c,f}(n,\theta,\phi)$.

For boundary estimation, the following are defined:

$$A_{1,v} \equiv \left\{ k \middle| \frac{1}{751} \sum_{m=0}^{750} \hat{f}_{c,f}(n+m, \theta(k), \phi(v)) \geq f_{u1} \text{ for all } n \in [750, 1250] \right\}. \tag{10}$$

$$A_{2,v} \equiv \left\{ k \middle| \frac{1}{251} \sum_{m=0}^{250} \hat{f}_{c,f}(n+m, \theta(k), \phi(v)) < f_1 \text{ for any } n \in [875, 1875] \right\}, \tag{11}$$

and $$A_{3,v} \equiv \left\{ k \middle| \frac{1}{1001} \sum_{n=1000}^{2000} \hat{f}_{c,f}(n, \theta(k+m), \phi(v)) > f_{u2} \text{ for all } m \in \{-1, 0, 1\} \right\}, \tag{12}$$

where $f_{u1}=1.38$ MHz. Equivalently $f_1 \equiv 0$, $f_{u2} \equiv \infty$, $A_{2,v}$ and $A_{3,v}$ are empty, and the adjusted heart tissue set $A_{h,v} \equiv A_{1,v}$.

The boundary angle between heart and lung in the v-th plane is $$\theta_b(v) \equiv \begin{cases} \theta(1) - \frac{1}{2}\Delta\theta & \text{if } A_{h,v} \text{ is empty} \\ \theta(40) + \frac{1}{2}\Delta\theta & \text{if } \max(A_{h,v}) \geq 40 - \frac{3-1}{2} = 39 \\ \theta[\max(A_{h,v})] + \frac{1}{2}\Delta\theta & \text{otherwise} \end{cases} \tag{13}$$

A 5-tap median filter (a function of v) in the elevational direction is then applied to $\hat{\theta}_b(v)$ and the output is denoted as $\hat{\theta}_{b,f}(v)$. From the filtered boundary angles $\hat{\theta}_{b,f}(v)$, a map indicating heart region can be derived to provide cross-plane visualization. To remove outliers around the boundary between heart and lung which appear occasionally, only the largest connected region is displayed. The clinician can use the FIG. 4B display to interactively manipulate the probe 130 so as to avoid the lung, in step S226.

An apparatus includes an imaging probe and is configured for dynamically arranging presentation of visual feedback for guiding manual adjustment, via the probe, of a location, and orientation, associated with the probe. The arranging is selectively based on comparisons between fields of view of the probe and respective results of segmenting image data acquired via the probe. In an embodiment, the feedback does not include a grayscale depiction of the image data. Coordinate system transformations corresponding to respective comparisons may be computed. The selecting may be based upon and dynamically responsive to content of imaging being dynamically acquired via the probe.

In addition to making diagnostic cardiac examination performable by nurses or other clinicians who may be untrained specifically in sonography, the apparatus 100 can guide novice sonographers. The apparatus 100 can feature, for this purpose or this mode, a regular (grayscale) sonogram, along with the visual feedback 144 described herein above. Alternatively, the novel visual feedback 144 of the apparatus 100 can speed up the work flow of trained or experienced sonographers.

While the invention has been illustrated and described in detail in the drawings and foregoing description, such illustration and description are to be considered illustrative or exemplary and not restrictive; the invention is not limited to the disclosed embodiments.

For example, the probe cable 140 may be omitted in a wireless probe embodiment.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. Any reference signs in the claims should not be construed as limiting the scope.

A computer program can be stored momentarily, temporarily or for a longer period of time on a suitable computer-readable medium, such as an optical storage medium or a solid-state medium. Such a medium is non-transitory only in the sense of not being a transitory, propagating signal, but includes other forms of computer-readable media such as register memory, processor cache, RAM and other volatile memory.

A single processor or other unit may fulfill the functions of several items recited in the claims. The mere fact that certain measures are recited in mutually different dependent claims does not indicate that a combination of these measures cannot be used to advantage.

What is claimed is:

1. An apparatus comprising:
   an imaging probe; and
   a user-guidance processor configured for dynamically arranging presentation of visual feedback for guiding manual adjustment, via said probe, of a location and orientation associated with said probe,
      wherein said arranging is based on comparisons between fields of view of said probe and respective results of segmenting image data acquired via said probe,
      wherein said feedback includes an instruction to halt based on an outcome of a comparison between a current location and current orientation of said probe and a location and orientation derived from said segmenting, wherein the user-guidance processor is configured to receive a first image obtained by the imaging probe in a first field of view of the imaging probe, wherein the user-guidance processor is configured to detect a pause in manual adjustment of the imaging probe, and wherein the user-guidance processor is configured to segment the first image during the pause to identify an anatomical segment of an organ within the first image.

2. The apparatus of claim 1, wherein said segmenting is model-based.

3. The apparatus of claim 1, wherein said imaging probe comprises an ultrasound imaging probe.

4. The apparatus of claim 1, further comprising a display configured for the presenting and dynamically guiding a user in a procedure for achieving an apical view of a heart.

5. The apparatus of claim 1, wherein at least one of the fields of view is three-dimensional.

6. The apparatus of claim 1, wherein a field of view from among said fields of view includes a viewpoint coinciding with said location, said orientation coinciding with a viewing orientation of said field of view.

7. The apparatus of claim 1, further comprising:
a display; and
a user-operable console,
said apparatus configured for:
acquiring said image data via said probe;
said segmenting;
displaying said feedback via said display; and,
portability as a hand-carriable unit.

8. The apparatus of claim 7, further configured for, responsive to detecting that said halting has occurred, performing said segmenting.

9. The apparatus of claim 1, wherein said feedback comprises a progressive indicator of overall progress in acquiring a target view.

10. The apparatus of claim 1,
wherein the user-guidance processor is configured to determine an orientation of the anatomical segment in the first field of view, and
wherein determining the orientation comprises comparing the anatomical segment to a model representative of the organ.

11. The apparatus of claim 1, wherein the user-guidance processor is configured to determine a second field of view of said imaging probe based on an orientation of the anatomical segment and the first field of view.

12. The apparatus of claim 11, wherein the second field of view comprises a different orientation of the anatomical segment from the first field of view.

* * * * *